United States Patent [19]

Cole et al.

[11] Patent Number: 5,060,521

[45] Date of Patent: Oct. 29, 1991

[54] REVERSE-DIRECT STRESS TESTING DEVICE

[75] Inventors: David M. Cole, Lyme; Larry D. Gould, Canaan, both of N.H.

[73] Assignee: The United States of America as represented by the Secretary of the Army, Fort Belvoir, Va.

[21] Appl. No.: 391,903

[22] Filed: Aug. 10, 1989

[51] Int. Cl.⁵ ............................................. G01N 3/02
[52] U.S. Cl. ..................................................... 73/857
[58] Field of Search ................. 73/857, 859, 856, 831, 73/833, 837, 834, 826, 830

[56] References Cited

FOREIGN PATENT DOCUMENTS 10573  1/1980  Japan ..................................... 73/856
539257 12/1976  U.S.S.R. ................................. 73/857

Primary Examiner—Jerry W. Myracle
Attorney, Agent, or Firm—Darrell E. Hollis

[57] ABSTRACT

A clamping device for applying loads to a test specimen including spherical segments connected to ends of the specimen. The spherical segments are in turn gripped by a race which allows pivotal movement of the segment. When the system is activated the race is gripped by the collet which is radially deformed by a circumferential clamp. When the spherical segment is clamped securely by the clamping device, the specimen may be axially or torsionally loaded by a reverse-direct stress testing device to determine physical properties of the specimen.

11 Claims, 3 Drawing Sheets

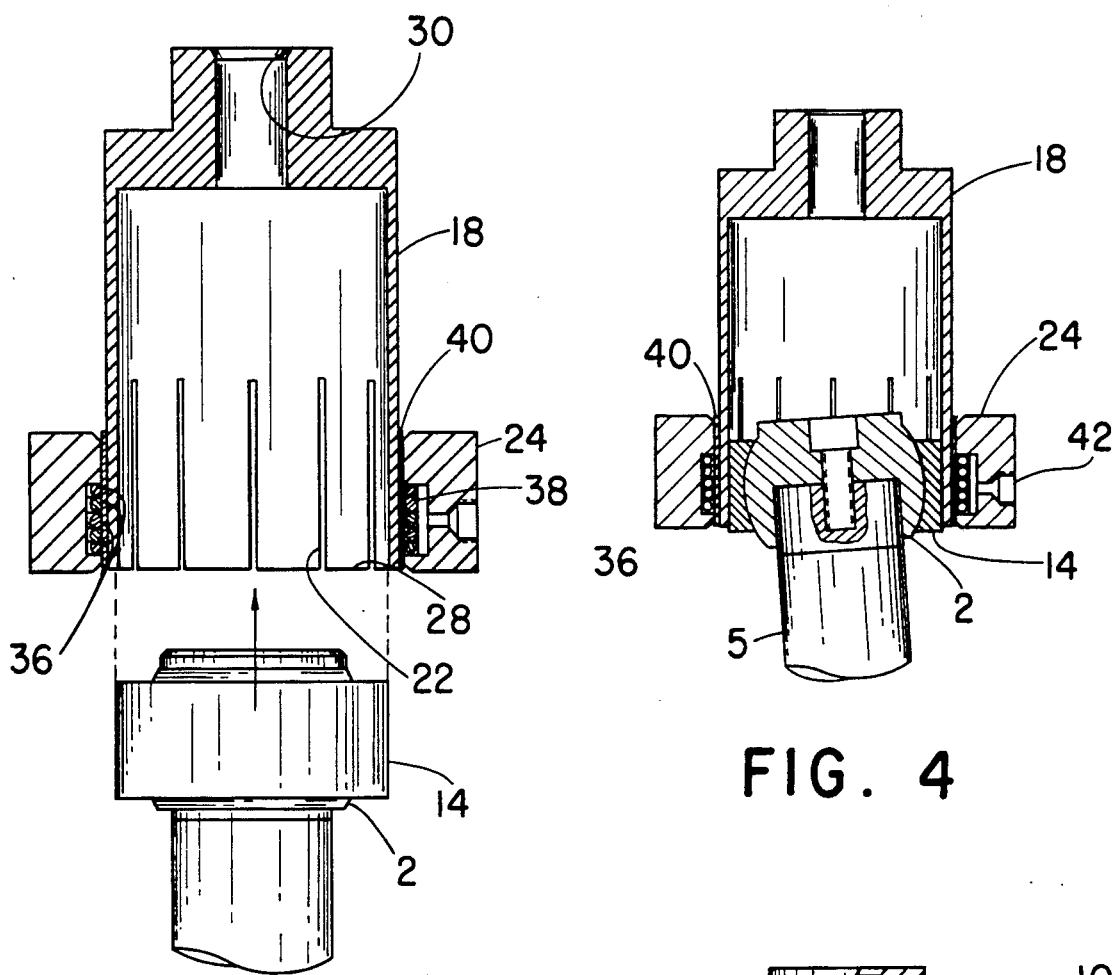
FIG. 3
FIG. 4
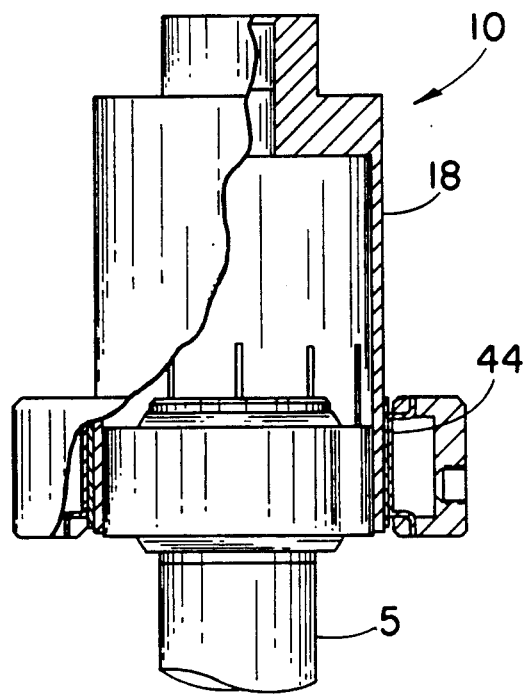
FIG. 5

REVERSE-DIRECT STRESS TESTING DEVICE

STATEMENT OF GOVERNMENT INTEREST

The invention described and claimed herein may be manufactured and used by or for the Government of the United States of America for governmental purposes without the payment of royalties thereon or therefor.

FIELD OF THE INVENTION

This invention relates to a clamping fixture of a stress testing device which is characterized by a spherical segment which can be affixed to either end of the test specimen to facilitate axial loading of the specimen by the stress testing device.

BACKGROUND OF THE INVENTION

The design requirements for this clamping fixture stem from the need to accommodate small degrees of misalignment in brittle specimens which are to be subjected to fully reversed axial or torsional loads. Important information of the mechanical properties of a material can be obtained from uniaxial tests in which the stress or strain can be cycled freely between tension and compression. For example, damping and deformation mechanisms, modulus variations and cyclic stress-induced damage can be studied. The capability of fully reversing stress allows the examination of material behavior under loading paths which cannot be attained by other experimental methods.

Despite the usefulness of the reversed direct stress techniques, its application has generally be been limited to easily machined manufactured materials. The application of this technique to more brittle materials and specimens of geologic materials, such as ice, has been hampered by the difficulties associated with rigidly fixing the specimen in a loading device. It is difficult to mount a material having relatively low fracture strength in a stress testing device. Misalignment or geometric imprecision common in specimens of naturally-occurring materials must be accommodated by the test fixtures in order to avoid damage or complete mechanical failure of the test piece will occur while it is being attached to the testing machine.

Hydraulically-actuated systems for gripping slightly misaligned specimens of brittle materials exist. These systems generally employ a ball seat to correct for specimen misalignment, but are designed for a very narrow range of specimen geometries and are generally very expensive. The current state-of-the-art systems have in common the feature that the ball seat used for correction of the alignment error is located at some distance from the source of the error, not at the specimen itself. When even the lightest misalignment is corrected for in this manner, the stress state in the test piece deviates from the intended pure stress field. This condition can seriously affect the validity of the test results.

In view of the above, it can be seen that there is a need for a device which allows for rapid and precise gripping of a test specimen in a stress testing device which avoids the introduction of unintended bending moments or axial loads to the specimen.

OBJECTS AND SUMMARY OF THE INVENTION

It is a primary object of the invention to provide a clamping fixture which will accommodate small degrees of misalignment in brittle specimens which are to be subjected to fully reversed axial or torsional loads in a stress testing device.

Another object of the disclosed invention is to provide a clamping fixture which introduces no axial loads or bending moments to the test specimen upon actuation of the clamping force.

Yet another object of the disclosed invention is a unique self-aligning feature which avoids the introduction of unintended bending moments or axial loads to the specimen.

A further object of the disclosed invention is to provide a system which is relatively uncomplicated and consists of a small number of components.

Yet another object of the disclosed invention is to provide a gripping system which is relatively compact in size, lending itself to use in pressure vessels or environmental chambers.

Another object of the disclosed invention is to provide a clamping fixture which will accommodate misalignment or geometric imprecision common in specimens of naturally-occurring materials.

Yet another object of the disclosed invention is to provide a clamping fixture which will operate at relatively low temperatures and its operation will be efficient enough to allow for specimen mounting times of one minute or less.

In summary, therefore, this invention is directed to a specimen clamping device for accommodating small degrees of misalignment in brittle specimens which are to be subjected to fully-reversed axial or torsional loads. The clamping device is currently configured for operation on a servo-controlled electro-hydraulic testing system and requires a hydraulic pressure source for operation of the preferred embodiment. The actual gripping mechanisms are relatively compact and would readily lend themselves to applications on other test systems.

These and other objects and advantages of the invention will be readily apparent in view of the following description and drawings of the above described invention.

DESCRIPTION OF THE DRAWINGS

The above and other objects and advantages and novel features of the present invention will become apparent from the following detailed description of the invention illustrated in the accompanying drawings, wherein:

FIG. 3 is an assembly showing the collet in cross section with the specimen holder (fragmentary) about to be loaded therein.

FIG. 4 is a cross sectional view of the collet and the spherical segment showing the specimen ice being supported; a portion of which is broken away and wherein the spherical segment accommodates a geometrically misaligned ice specimen.

FIG. 5 is a top plan view with portions shown in section of a second embodiment having a flexible membrane to transmit the clamping force to the spherical segment in place of O-rings.

DESCRIPTION OF THE INVENTION

Figure 1:
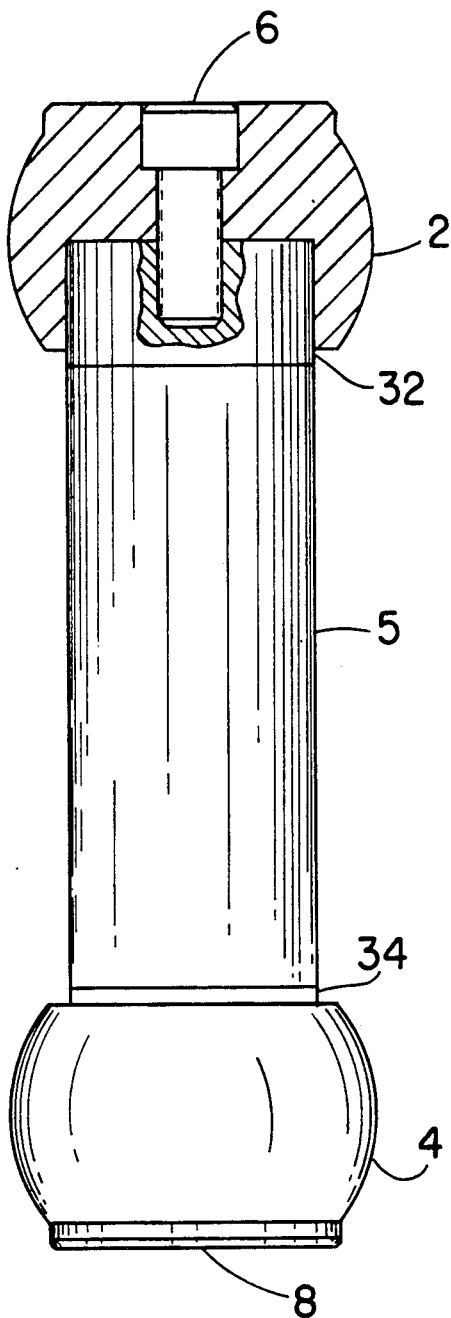
FIG. 1 is a top plan view of the spherical segments attached to end caps which are bonded to a cylindrical specimen, with one spherical segment shown in cross section.

A shown in FIG. 1, a test specimen S is held between two precision ground spherical segments 2 and 4. Each spherical segment is bolted to one end of the specimen S by bolts 6 and 8. Spherical segments 2 and 4 are constructed of a high quality ground and hardened ball segment which reacts against the clamping force exerted through the other components of the system, but transmits no fraction of that force to the specimen S.

Figure 2:
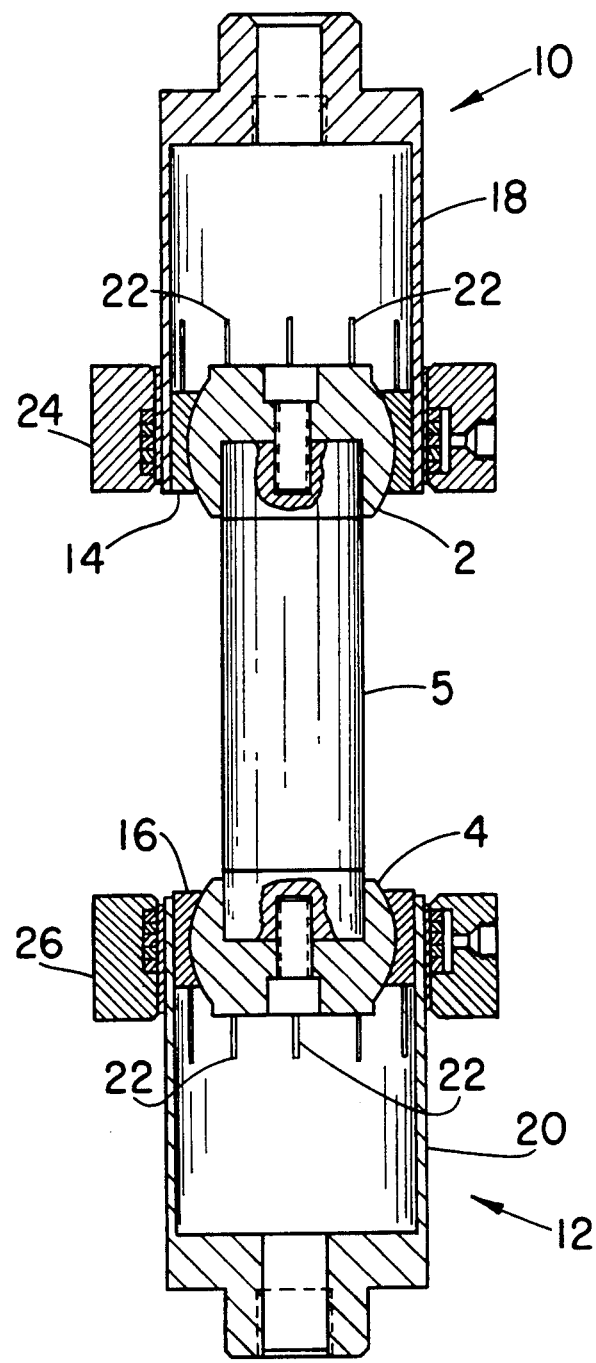
FIG. 2 is a cross sectional view of the spherical segments engaged with the clamping members of a stress testing device with portions of the specimen broken away to reveal the connection bolt.

FIG. 2 illustrates the specimen S and spherical segments 2 and 4 held in by clamping members 10 and 12. Each of spherical segments 2 and 4 is held in position by races 14 and 16, respectively. Each of the races 14 and 16 extends around its associated spherical segment 2 and 4, respectively. Races 14 and 16 are shown as placed inside cylindrical collets 18 and 20, respectively. Race 14 and 16 have been cut along 8 radii (not shown) such that only very narrow ligaments remain along the outer fiber. These cuts serve to increase the radial compliance of races 14 and 16, thereby allowing the clamping force to be more directly transmitted to spherical segments 2 and 4. Each of collets 18 and 20 have therein saw cuts 22 which permit radial deformation of collets 18 and 20 when clamping force is applied by circumferential clamps 24 and 26, respectively.

As best shown in FIG. 3, collet 18 is formed into an elongated cylindrical shape having an open end 28 for receiving race 14 and spherical segment 2. Collet 18 further includes opening 30 at the end of collet 18 opposite opening 28.

When race 14 is inserted into collet 18, race 14 is free to slide inside collet 18. Spherical segment 2 is also free to rotate with respect to collet 14 and further is free to pivot perpendicularly to the axis of rotation. This combination of pivotal movement combined with rotational movement allows spherical segment 2 to rotate as required to fully accommodate the misalignment of the specimen S prior to pressurization of the system. Races 14 and 16 and their respective spherical segments 2 and 4 remain together as a unit throughout operation of the device.

Spherical segments 2 and 4 are bolted to respective end caps 32 and 34 mounted on specimens S as best shown in FIG. 1. The specimen S can be loaded axially provided that end caps 32 and 34 are centered on the specimen. If end caps 32 and 34 are not centered, off axis loading will result. In either event, however, the device accommodates the fact that the faces of the end caps 32 and 34 may not be parallel with each other or perpendicular to the center line of the specimen. FIG. 4 shows correction for a misaligned specimen S by spherical segment 2 and race 14.

As best shown is FIG. 3, the preferred embodiment includes a circumferential clamp 24 having a chamber C having a series of O-rings which may be pressurized along their outer faces 38. Clamp 24 also includes sleeve 40 which is a thin-walled cylinder preferably having a series of saw cuts (not shown) parallel to the cuts 22 in collet 18 to accommodate a certain degree of radial deformation. The saw cuts (not shown) have been filled with a thermoplastic which allows some deformation but prevents extrusion of O-rings 36 upon pressurization. Sleeve 40 could also be made from a solid piece of appropriate material.

Hydraulic pressure is applied through port 42 in clamp 24 as best shown in FIG. 4. O-rings 36 act against sleeve 40 which compresses slightly when hydraulic pressure is applied to the system. Since each O-ring 36 contributes equally to the clamping force, the total clamping force can be increased by adding additional O-rings 36. The total clamping force is determined approximately by multiplying the wetted area of O-rings 36 by the hydraulic pressure applied. Collet 18 is in turn compressed by the deformation of the sleeve and securely grips the bearing race 14. When hydraulic pressure is applied to the system, the radial compressive stress is sufficient to lock spherical segment 2 in place in the race 14 and also locks race 14 within collet 18. Spherical segment 4 reacts against the clamping force exerted through race 14, but transmits no fraction of that force to the specimen. In a pressurized, but yet unloaded state, collet 18 serves to hold circumferential clamp 34 and sleeve 40 in position. Collet 18 transmits axial loads from the testing machine (not shown) to the specimen when the system is activated.

In order to test a specimen, it must be suitably mounted in spherical segments 2 and 4. This requires bonding to end caps 32 and 34, if end caps are to be used, and bolting of spherical segments 2 and 4 to the ends of speciment S.

Preferably, the spherical segments 2 and 4 are constructed of hardened metal or suitably rigid plastic materials or the like. O-rings 36 and flexible membrane 44 are preferably constructed of rubber of flexible plastic materials or the like. Collets 18 and 20 and races 14 and 16 are preferably constructed of relatively rigid materials, but having some degree of elasticity, such as metal or plastic. Spherical segments 2 and 4 are then inserted into their respective races 14 and 16. Each race 14 and 16 is inserted into its respective collet 18 and 20 and test specimen S is positioned to correct for misalignment or geometric imprecision of the specimen which is common in specimens of naturally occurring materials such as ice. After the specimen S is suitably mounted, clamps 24 and 26 are pressurized simultaneously or sequentially and the system is then ready for loading. Pressurization transmits no force to specimen S. After testing, the hydraulic pressure is released and spherical segments 2 and 4 are removed from their respective clamping devices 10 and 12.

FIG. 4 illustrates proper alignment of a specimen S having a tilted end cap 32. Note that spherical segment 2 is rotated as required by end cap 32 positioning and can be firmly clamped. FIG. 4 shows a somewhat exaggerated rotation of about 4 degrees for visual affect. Actual rotations are typically less than 0.1 degrees.

Another embodiment of the invention is shown in FIG. 5. In this embodiment, a fully confined flexible membrane 44 is used in place of the O-ring assembly 36 of the preferred embodiment.

Figure 6:
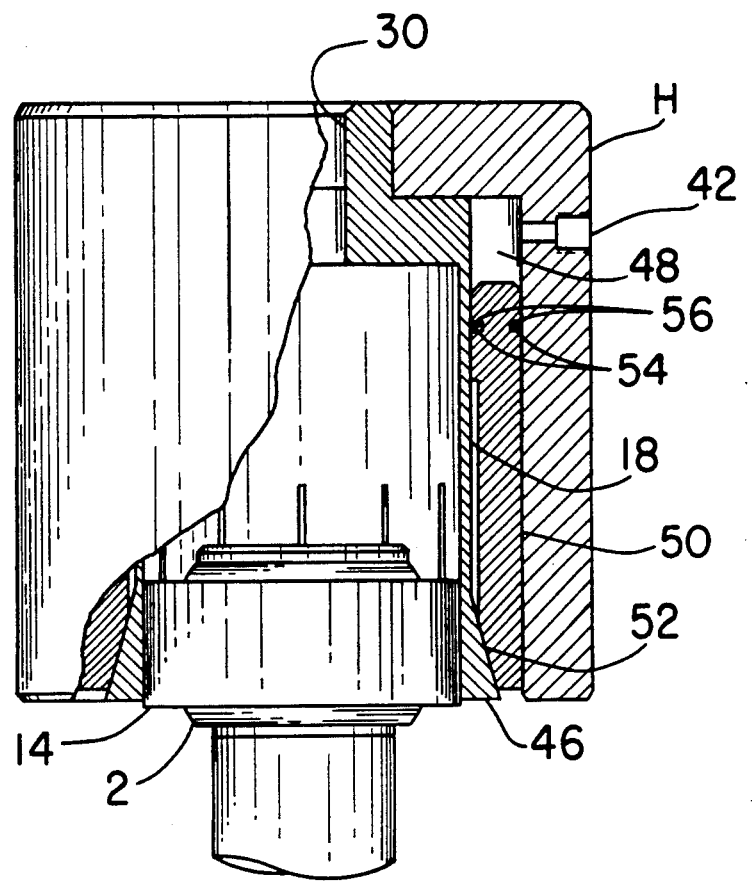
FIG. 6 is a top plan view of the collet and spherical segment shown partially in section of a third embodiment which uses hydraulic pressure to compress the collet via a tapered ring.
Figure 7:
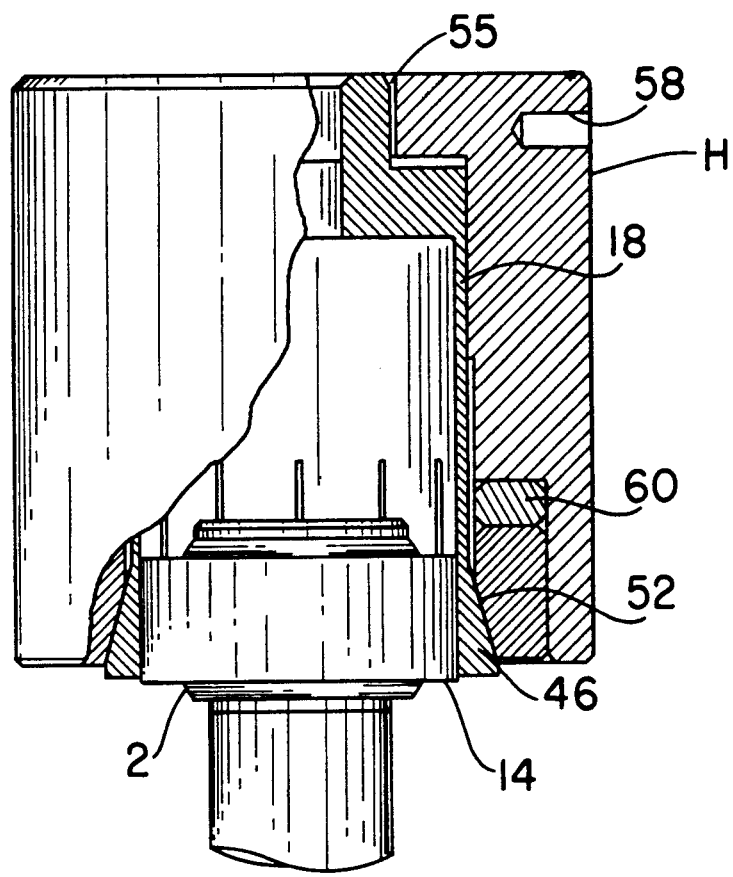
FIG. 7 is a top plan view of the collet and spherical segment of a fourth embodiment which uses a threaded collar to drive the tapered ring to transmit the clamping force.

FIGS. 6 and 7 illustrate other embodiments of the invention wherein collet 18 includes a tapered portion 46 extending outwardly at opening 28. In FIG. 6, a housing H is connected to collet 18 near opening 30. Housing H forms an open chamber 48 between housing H and collet 18. A ring 50 having a tapered surface 52 in complementary registration with tapered edge 46 of collet 18 is located in the chamber 48 between housing H and collet 18. Pressure seals 54 are placed in slots 56 to prevent leakage when hydraulic pressure is applied through port 42. The application of pressure through port 42 acts to force ring 50 axially along collet 18 in a direction away from opening 30. Movement of ring 50 causes tapered edge 52 to exert a radially deforming force upon tapered edge 46 of collet 18. The force applied by ring 50 and tapered edge 52 acts upon collet 18 to securely grip race 14 and spherical segment 2.

Another embodiment of the invention is shown in FIG. 7 which does not require the use of hydraulic pressure. Housing H is rotatably attached to collet 18 at a threaded collar 55. Housing H may be rotated by use of a spanner wrench (not shown) inserted in spanner wrench hole 56. Rotation of housing H causes movement of housing H relative to collet 18 and tapered surface 52 of thrust bearing 60 which forms a part of housing H to contact tapered surface 46 of collet 18 to radially deform collet 18 and apply gripping force to race 14 to grip spherical segment 2.

While this invention has been described as having a preferred embodiment, it is to be understood that it is capable of further modification, and uses and/or adaptations of the invention which follow in general the principle of the invention and including such departures from the present disclosure as common within known or customary practice in the art to which the invention pertains, and as may be applied to the central features herein before set forth, and fall within the scope of the invention and the limits of the appended claims.

What we claim is:

1. A clamping device for gripping a test specimen comprising:
   (a) specimen gripping means including a spherical segment for connection the test specimen and an end cap affixed to the specimen;
   (b) means for attaching said specimen gripping means to means for applying an axial or torsional load to said specimen gripping means;
   (c) said specimen gripping means including means for correction of alignment error such that introduction of unintended bending moments or axial loads is avoided.

2. The clamping device of claim 1, wherein:
   (a) said means for correction of alignment error includes race means in pivotal connection with said spherical segment.

3. The clamping device of claim 2, wherein:
   (a) said specimen gripping means includes a collet;
   (b) said collet forming a cylindrical shape having first and second ends;
   (c) an opening at said first end for reception of said race means; and,
   (d) means at said second end for connection to the load applying means.

4. The clamping device of claim 3, wherein:
   (a) said collet further including a series of cuts therein at said first end;
   (b) said series of cuts provide accommodation for elastic radial deformation of said first end when a clamping force is applied thereon.

5. The clamping device of claim 4, wherein:
   (a) said clamping device includes a pair of specimen gripping means.

6. The clamping device of claim 4, wherein:
   (a) said specimen gripping means includes a thin-walled cylindrical sleeve; and,
   (b) said sleeve encircles and contacts said first end of said collet.

7. The clamping device of claim 6, wherein:
   (a) said specimen gripping means includes circumferential clamping means;
   (b) said circumferential clamping means includes means for receiving a hydraulic pressure supply;
   (c) said circumferential clamping means including hydraulic pressure applying means for selectively applying force to said sleeve and said collet to exert a gripping force on said race.

8. The clamping device of claim 7, wherein:
   (a) said hydraulic pressure applying means comprises a plurality of O-rings.

9. The clamping device of claim 7, wherein:
   (a) said hydraulic pressure applying means comprises a fully confined flexible membrane.

10. The clamping device of claim 4, wherein:
    (a) said collet further forms a tapered portion at said first end thereof;
    (b) said tapered portion extends outwardly of said opening;
    (c) a tapered ring;
    (d) said ring surrounding said collet and having a tapered end in complementary registration to said tapered end of said collet;
    (e) a housing;
    (f) said housing extending around said ring and engaging said collet at said second end.
    (g) said housing including means for receiving hydraulic pressure;
    (h) a chamber;
    (i) said chamber being bounded by said housing and said collet and said tapered ring;
    (j) said ring being movable to bear against said tapered portion to apply force against said collet to radially deform said collet such that a gripping force is applied to said race to grip said spherical segment when hydraulic pressure is applied.

11. The clamping device of claim 4, wherein:
    (a) said collet further includes a tapered portion at said first end;
    (b) said tapered portion extends outwardly of said opening;
    (c) said clamping device further includes a housing;
    (d) said housing encircling said collet and being threadably connected to said second end of said collet;
    (e) said housing extending to said first end of said collet and engages said collet by means of a thrust bearing embedded in said housing;
    (f) said housing being mounted for peripheral and axial movement relative to said collet; and,
    (g) said housing being movable in a direction towards said first end upon rotation of said housing about said screw thread thereby causing said thrust bearing to engage said tapered portion to apply force to said collet to deform said collet to exert a gripping force on said race and thereby grip said spherical segment.

* * * * *